United States Patent [19]
Ryan

[11] Patent Number: 5,366,463
[45] Date of Patent: Nov. 22, 1994

[54] ATHERECTOMY CATHETER FOR THE REMOVAL OF ATHEROSCLEROSIS FROM WITHIN BLOOD VESSELS

[76] Inventor: William J. Ryan, 10670 Rosewood Ct., Pinellas Park, Fla. 34666

[21] Appl. No.: 27,221

[22] Filed: Mar. 5, 1993

Related U.S. Application Data

[63] Continuation-in-part of Ser. No. 896,736, Jun. 9, 1992, which is a continuation of Ser. No. 518,017, May 2, 1990, abandoned.

[51] Int. Cl.$^5$ .............................................. A61B 17/32
[52] U.S. Cl. ..................... 606/159; 606/170; 604/22
[58] Field of Search ............... 606/159, 170, 171, 180; 604/22

[56] References Cited

U.S. PATENT DOCUMENTS

| | | | |
|---|---|---|---|
| 1,162,014 | 1/1916 | O'Brien | 606/159 |
| 4,765,332 | 8/1988 | Fischell et al. | 606/159 |
| 4,867,156 | 9/1989 | Stack et al. | 606/159 |
| 5,011,490 | 4/1991 | Fischell et al. | 606/159 |
| 5,127,902 | 7/1992 | Fischell | 606/159 |
| 5,171,255 | 12/1992 | Rydell | 606/170 |

FOREIGN PATENT DOCUMENTS 0291170  11/1988  European Pat. Off. ............ 606/159

Primary Examiner—Stephen C. Pellegrino
Assistant Examiner—William W. Lewis
Attorney, Agent, or Firm—Pettis & McDonald

[57] ABSTRACT

An atherectomy catheter for the removal of atherosclerosis, thrombosis, cholesterol deposits, fatty nodules, and other such sclerotic material from within the blood vessels of a patient. According to a preferred construction, the catheter includes no moving parts, and the undesirable material is shaved from the entire inside diameter of the vessel and captured and removed therefrom by the application of negative pressure as the catheter is withdrawn along a longitudinal segment of the vessel. The catheter of this invention is characterized by the absence of any moving parts during the cutting process and its construction to permit removal of atherosclerosis with virtually no danger of harm to the vessel itself.

9 Claims, 6 Drawing Sheets

ATHERECTOMY CATHETER FOR THE REMOVAL OF ATHEROSCLEROSIS FROM WITHIN BLOOD VESSELS

This application is a continuation-in-part application of my co-pending application Ser. No. 07/896,736, filed Jun. 9, 1992, which was a continuation of my prior application Ser. No. 07/518,017, filed May 2, 1990, now abandoned.

FIELD OF INVENTION

The present invention relates to an atherectomy catheter for the removal of atherosclerosis from within the blood vessels of a patient. In its preferred embodiment, the invention is characterized by the absence of any moving parts while permitting even, smooth removal of atherosclerosis from within the vessel around the entire outside diameter of the catheter. In addition, the preferred embodiment further includes a source of negative pressure operatively connected to the substantially hollow interior of the catheter for the purpose of not only drawing the atherosclerosis into proximity with the catheter's cutting means, but also for safely removing severed material. Alternative embodiments including reciprocally-movable catheter parts are also disclosed.

DESCRIPTION OF THE PRIOR ART

Disorders of the arteries may be generally characterized as any condition which adversely affects the passage of blood through the arteries. The most common arterial disease, and the one which is most often a contributory cause of death, particularly in persons of advanced age, is arteriosclerosis, known as hardening of the arteries. The hardening is actually preceded by atherosclerosis, an accumulation of fatty deposits on the inner lining of the arterial wall. The deposits reduce the normal flow of blood through the artery. One of the best known substances associated with atherosclerosis is cholesterol. In addition, as a result of biochemical changes within the artery, scar tissue may develop, causing the artery wall to lose is elasticity and become prone to rupture. Atherosclerosis may affect any or all of the arteries of the body and is evidenced by symptoms in the organ or region of the body deprived of the proper supply of blood by the sclerotic condition. For example, if the blood vessels supplying the heart muscle are affected, the disease may lead to a heart condition known as angina pectoris.

Prior art literature and patents teach a number of techniques and devices for removing the fatty deposits leading to atherosclerosis and, ultimately, arteriosclerosis. According to the balloon catheterization technique, a catheter including an inflatable balloon element is placed in position next to a fatty deposit. The balloon is then inflated in an attempt to squash or flatten the fatty deposit/nodule sufficiently to open the artery so as to allow increased blood flow. Unfortunately, such fatty deposits are usually relatively sound, structurally, and resist this "flattening" pressure. In many instances, then, the use of a balloon catheter has only minimal effect on the fatty deposit. Of equal concern is the fact that inasmuch as the balloon catheter technique tends to stretch the artery, there is an inherent danger of splitting the scarred lining of the artery and, perhaps, inducing the equivalent of a burst aneurism. It is also recognized within the medical profession that the balloon catheter technique, when stretching the artery, also increases the risk of breaking off fragments of the fatty deposits, the presence of which in the blood stream could be extremely dangerous or even fatal to the patient.

Another technique for treating atherosclerosis is to utilize a catheter having a separable stainless steel wire mesh spring. This spring, when positioned next to a fatty deposit, will spring open to push back the deposit into the artery wall, resulting in increased blood flow. However, the steel spring will remain within the artery forever, and will continue to push against what may be an already weakened artery wall. As with the balloon catheter technique, the wire mesh spring device and technique really does not remove fatty deposits, rather, it merely pushes them into the artery wall, necessarily stretching the wall, in an effort to obtain increased blood flow. As above, this technique subjects the patient to the danger of not only rupturing the artery wall, but also because the fatty deposit is not removed, the likelihood of a fragment becoming separated from the deposit and being carried into the bloodstream certainly is not decreased. In fact, that eventuality may actually be increased because of the pressure exerted by the spring.

Perhaps in recognition of the inescapable risks and deficiencies associated with both balloon catheters and wire mesh spring catheters, the prior art does disclose and teach catheter devices for removing such sclerotic materials by mechanical action. For example, U.S. Pat. No. 4,867,156, to Stack, et al., discloses a percutaneous axial atheroectomy catheter. According to the disclosure of Stack, this device is constructed so as to remove plaque by the action of a rotating first cutter as the device is pushed through the obstruction, and then to remove further plaque by the action of a rotating second cutter as the device is pulled rearwardly back through the obstruction. Means are also provided to capture and "hold" the removed material. U.S. Pat. No. 4,994,067 to Summers discloses a distal atherectomy catheter including a cutting burr for boring through obstructions in the vessel and means for reciprocating an inner catheter tube relative to an outer catheter tube for excising occlusive material in the vessel. Summers also discloses the use of a vacuum means to evacuate the excised occlusive material. U.S. Pat. No. 5,011,490 to Fischell, et al., also discloses an endoluminal tissue excision catheter system utilizing a driven, rotary cutter to excise obstructive tissue. The Fischell patent also discloses a tissue collection chamber formed within the cylindrical cutting blade for the purpose of containing the excised tissue. According to the disclosure of Fischell, that device includes both a collect catheter and a closing catheter with the closing catheter adapted to move slidably along the collect catheter so as to secure the cut tissue within the collection chamber. Still another such device is disclosed in U.S. Pat. No. 5,026,384, to Farr, et al. According to the disclosure of that patent, a rotating cutter on the distal end of a torque tube extends into the obstruction and bores or cuts its way therethrough. Vacuum means are connected to the torque tube for extracting dislodged cuttings from the patient's bloodstream.

Thus, while it is clear that there are mechanical devices for removing atherosclerosis from blocked arteries, virtually all of those devices depend upon either a rotating cutter or a pair of reciprocating elements to accomplish the cutting action. It is also to be noted that while at least some of the prior art devices disclose the use of a vacuum for removing severed material, none of the prior art discloses or suggests that the vacuum may be used in cooperation with an essentially stationary, fixed cutting means actually to "pull" the undesired material into contact with the cutter. In fact, most of the prior art depends upon stretching the artery and "mashing" the cutter against the occlusion material, rather than somehow forcing the occlusion into contact with the cutter. Notwithstanding the number and sophistication of prior art atherectomy catheters, it is clear that there still remains a great need for such a catheter which is of extremely simple construction, which "pulls" the undesirable material into contact with the cutter rather than stretching the vessel and forcing the cutter into the plaque, and which may also include positive means for evacuating the removed material from the patient's bloodstream.

SUMMARY OF THE INVENTION

The present invention relates to an atherectomy catheter for the removal of atherosclerosis from within the blood vessels of a patient. In its preferred embodiment, the catheter of this invention is characterized by a substantially hollow catheter body mounted on a guide wire with the guide wire and the catheter body being insertable into a vessel from which atherosclerosis is to be removed. The body comprises a substantially rigid tip and a flexible segment remote from the tip, the flexible segment being attached to the tip such that a circumferential gap is provided in the body between the tip and the flexible segment. A cutting means is operatively disposed in the circumferential gap so that manipulation of the catheter body will cause the cutting means to remove atherosclerosis from the interior of the vessel all around the outer circumference of the catheter. Removed material is directed into the hollow catheter body for disposal, preferably by the action of a vacuum means. In this preferred embodiment, the catheter of this invention has literally no moving parts and can therefore be fabricated quite easily to define a diameter of less than two mm. By virtue of its small size and lack of moving parts, there is a substantial reduction in the likelihood of the catheter's causing damage to the media of the artery from which the sclerotic material is being removed. Application of a vacuum to the hollow body of the catheter serves to "pull" the artery wall toward the cutting means, thereby virtually eliminating the likelihood that the artery wall will stretch which would, of course, not only subject the artery to weakening, but also might dislodge sclerotic material into the bloodstream.

Throughout the disclosure and description of this invention, it is to be understood that the term "atherosclerosis" is intended to encompass not only atherosclerosis, per se, but also thrombosis, cholesterol deposits, fatty nodules, and other such occlusion-type diseases of arteries, veins and other tubular areas of the body.

The invention accordingly comprises the features of construction, combinations of elements, and arrangements of parts which will be exemplified in the constructions hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

Similar reference characters refer to similar parts throughout the several views of the drawings.

DETAILED DESCRIPTION

Figure 1:
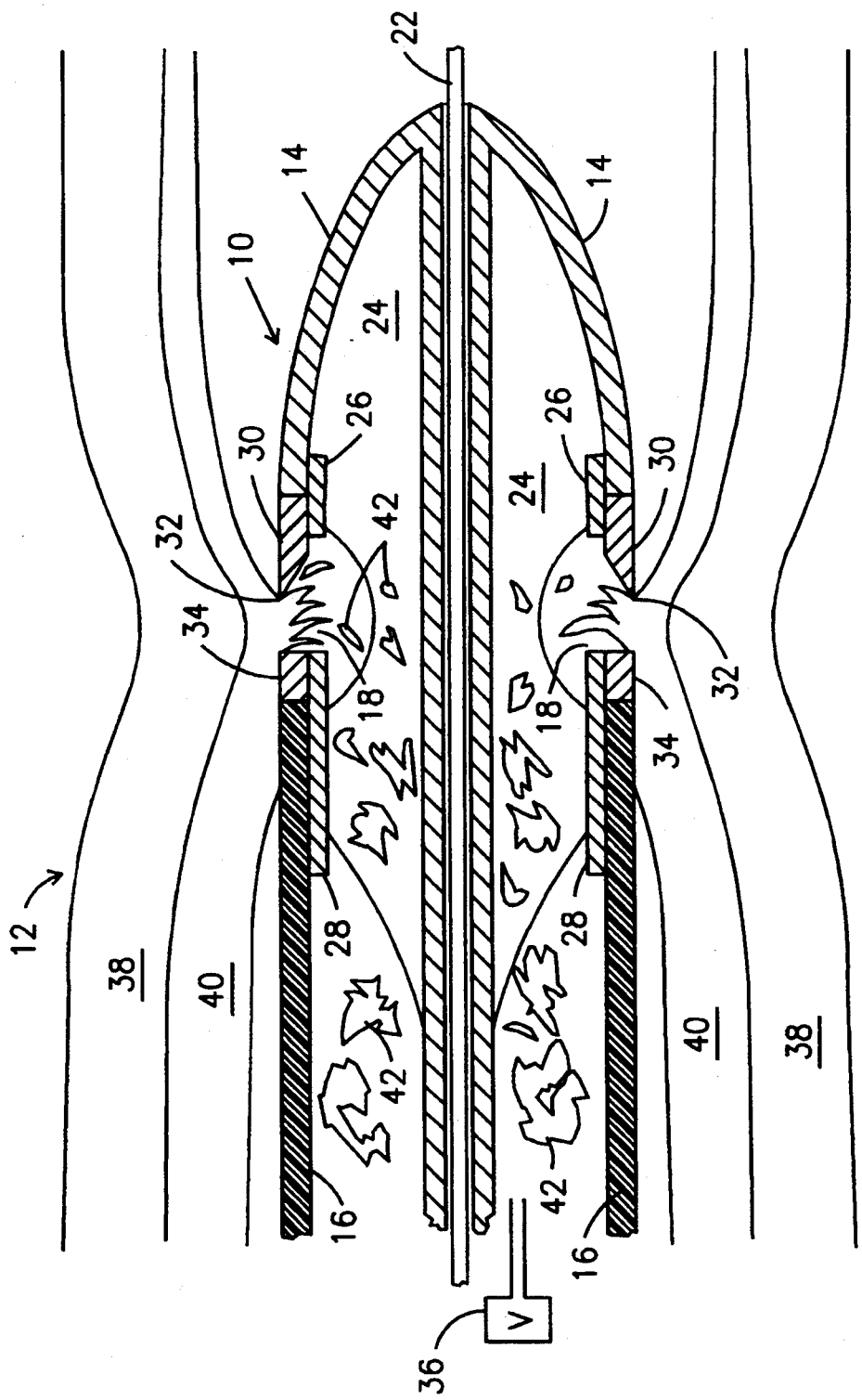
FIG. 1 is a sectional view of the distal, cutting end of a preferred embodiment of the atherectomy catheter of this invention operatively disposed within the blood vessel of a patient and showing the removal of atherosclerosis therefrom.
Figure 2:
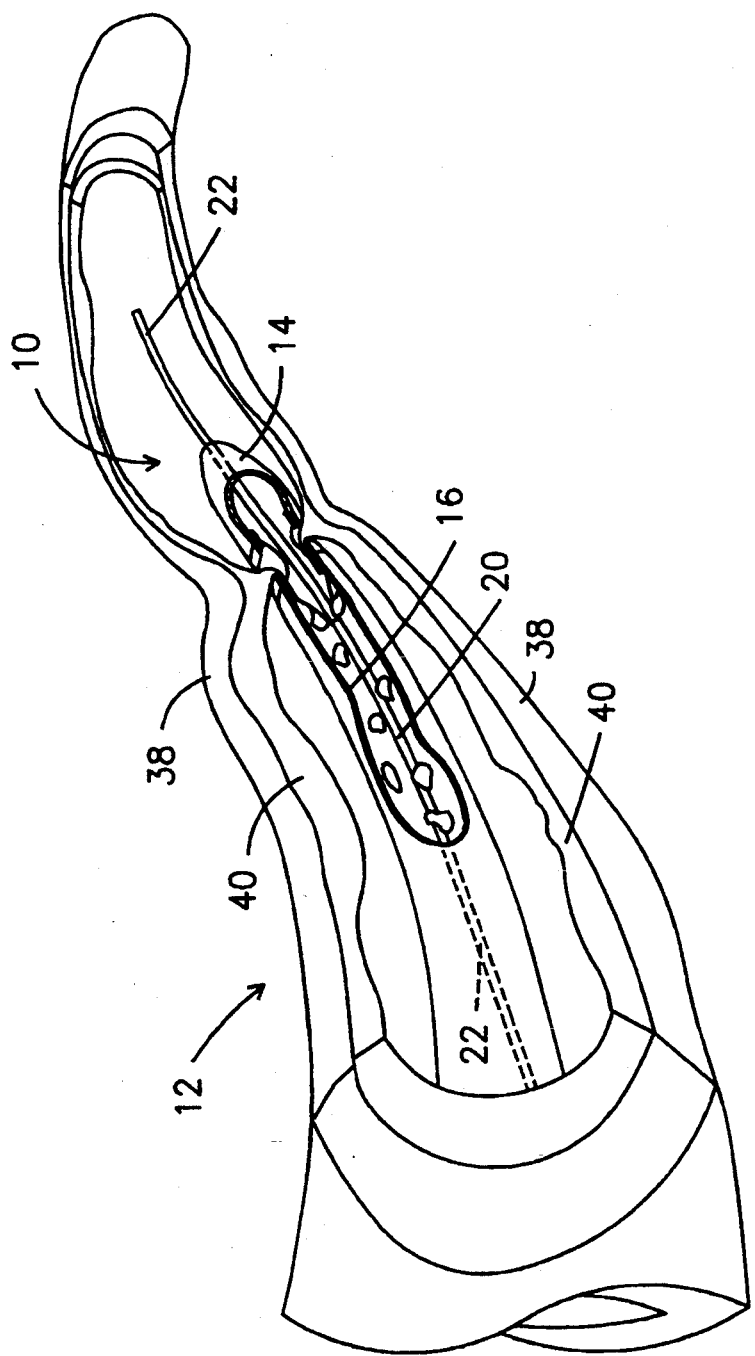
FIG. 2 is an enlarged view, partially in section, showing the preferred embodiment of the atherectomy catheter of this invention within the blood vessel of a patient.

Referring to the view of FIG. 2, one may see, in partial cutaway, a preferred embodiment of the atherectomy catheter of this invention, generally indicated as 10, operatively positioned within a blood vessel generally indicated as 12. Further details of the preferred catheter 10 are provided in the sectional view of FIG. 1. As shown in the view of FIG. 1, catheter 10 comprises a substantially hollow catheter body including a rigid tip 14 and a flexible segment 16, with segment 16 being attached to tip 14 so as to define a circumferential gap 18 therebetween. A lumen 20 extends along the midpoint of catheter 10 and is an integral portion of tip 14. As clearly seen in the views of FIGS. 1 and 2, a guide wire 22 passes through lumen 20, and guide wire 22 is used to insert and position the catheter 10.

Referring again to the sectional view of FIG. 1, it can be seen that tip 14 and segment 16 are connected one to the other by a plurality of internal braces 24. While two of the braces 24 are shown in the sectional view of FIG. 1, in the preferred embodiment for catheter 10, there would be a total of four such braces 24, each of them oriented to another at a substantial 90° angle. Actual attachment of each brace 24 to tip 14 is accomplished by a corresponding one of the tip anchors 26, and attachment of each brace 24 to flexible segment 16 is provided through a corresponding one of the tubing anchors 28.

A substantially circular cutting means 30 is operatively disposed on tip 14 within the gap 18 such that cutting edge 32 of means 30 is disposed rearwardly, toward flexible segment 16. The cutting means 30 is actually mounted to tip 14 by the plurality of internal braces 24 and the corresponding tip anchors 26 associated with each of the braces 24.

While each of the braces 24 is attached to a corresponding portion of flexible segment 16 by the tubing anchors 28, the view of FIG. 1 further illustrates the attachment of a substantially circular cutting ring guard spacer 34 at the distal end of flexible segment 16, adjacent gap 18.

Finally, a vacuum means 36 is operatively disposed in communicating relation with the hollow interior of catheter 10 and is operable to provide a negative pressure to the hollow interior of catheter 10, which will result in drawing portions of artery 38 and any atherosclerosis 40 adhered thereto into gap 18 for engagement by cutting edge 32 of the cutting means 30.

In operation and use, this preferred embodiment for catheter 10 is inserted into the patient's artery 38 by means of guide wire 22, as illustrated in the views of FIGS. 1 and 2. Catheter 10 is advanced along the artery until tip 14 and gap 18 have passed a region on the interior of artery 38 from which portions of atherosclerosis 40 are to be removed. A negative pressure is applied utilizing vacuum means 36, causing artery 38 and atherosclerosis 40 attached thereto to collapse inwardly into gap 18 as illustrated in the views of FIGS. 1 and 2. Then, utilizing known catheter manipulation techniques, catheter 10 is drawn rearwardly so that cutting edge 32 will engage and shave fragments 42 of atherosclerosis 40 from the wall, or media, of artery 38. Because of the negative pressure created by vacuum means 36, fragments 42 are quickly and safely contained within the hollow portion of catheter 10. Alternatively, means may be provided for actually withdrawing those fragments from catheter 10 while catheter 10 is still operative. Even though it is not intended that the view of FIG. 1 provides a drawing to precise scale, one may see that the relative thickness of atherosclerosis 40 in the vicinity of tip 14 is noticeably thinner than the deposits of atherosclerosis 40 adjacent flexible tubing 16. This is intended to illustrate use of catheter 10 for cutting/shaving atherosclerosis 40 from the interior of artery 38 as the catheter 10 is withdrawn.

Figure 3:
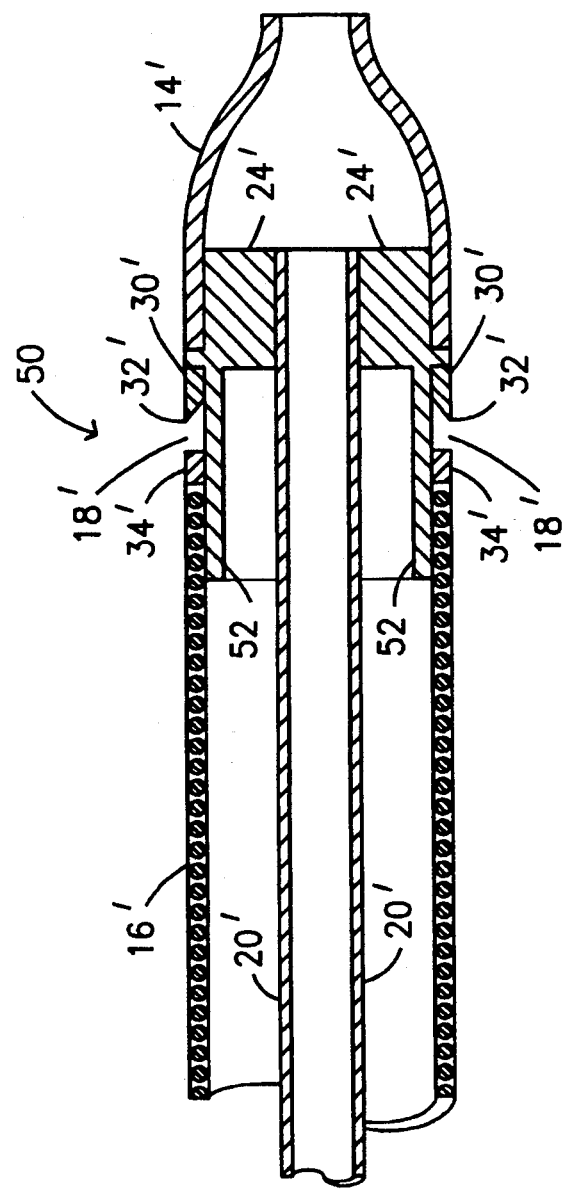
FIG. 3 is a sectional view of the distal, operative end of another embodiment of the atherectomy catheter of this invention.

Attention is now invited to the view of FIG. 3 wherein an alternative embodiment for the atherectomy catheter of this invention is shown and generally indicated as 50. According to this embodiment of catheter 50, it also defines a substantially hollow catheter body comprising a rigid tip 14' and a flexible segment 16'. Tip 14' and segment 16' are attached to each other by an internal brace 24' having a plurality of legs 52 formed thereon, with two of such legs shown in the view of FIG. 3. As a result, a circumferential gap 18' is provided between tip 14' and segment 16', with gap 18' in fluid-communicating relation to the hollow interior of this catheter 50. A cutting means 30' including a cutting edge 32' formed thereon is attached to tip 14' through internal brace 24', and a cutting ring guard spacer is attached to the distal end of segment 16' and leg portions 52 of brace 24'. A lumen 20' is also provided through the center of catheter 50 for insertion of a guide wire (not shown).

According to the preferred embodiment for catheter 10 shown in the views of FIGS. 1 and 2, and the alternate embodiment 15 of FIG. 3, tip 14/14' may be formed from any suitable material such as, for example, plastic or stainless steel. Flexible segment 16 of catheter 10 is preferably formed from a plastic material, while flexible segment 16' of catheter 50 is a plastic-coated stainless steel coil. Cutting means 30/30' may also be formed form any suitable material such as plastic or stainless steel, and the same is true of cutting ring guard spacer 34/34'.

It is to be understood that the relative sizes and placements of cutting means 30/30' and cutting ring guard spacers 34/34' will determine the depth of a cut made by cutting edges 32 and 32'. It is also to be understood that a vacuum means substantially identical to vacuum means 36 shown in combination with catheter 10 would also be incorporated into the structure of the alternative catheter 50. In addition, the use of catheter 50 is substantially identical to that briefly described above with regard to catheter 10. By virtue of the construction of catheters 10 and 50, one may appreciate the simplicity, safety, and efficiency with which atherosclerosis may be removed from the entire inside wall of a patient's blood vessel. Utilizing the negative pressure created by vacuum means 36, and as a result of the extremely small outside diameter (even less than 0.2 mm) of catheters 10 and 50, the likelihood of damaging the artery by stretching or inadvertently dislodging fragments of atherosclerosis is virtually eliminated. Utilization of either catheter 10 or 50 for the removal of atherosclerosis thus becomes a relatively non-invasive and mild surgical procedure.

Figure 4:
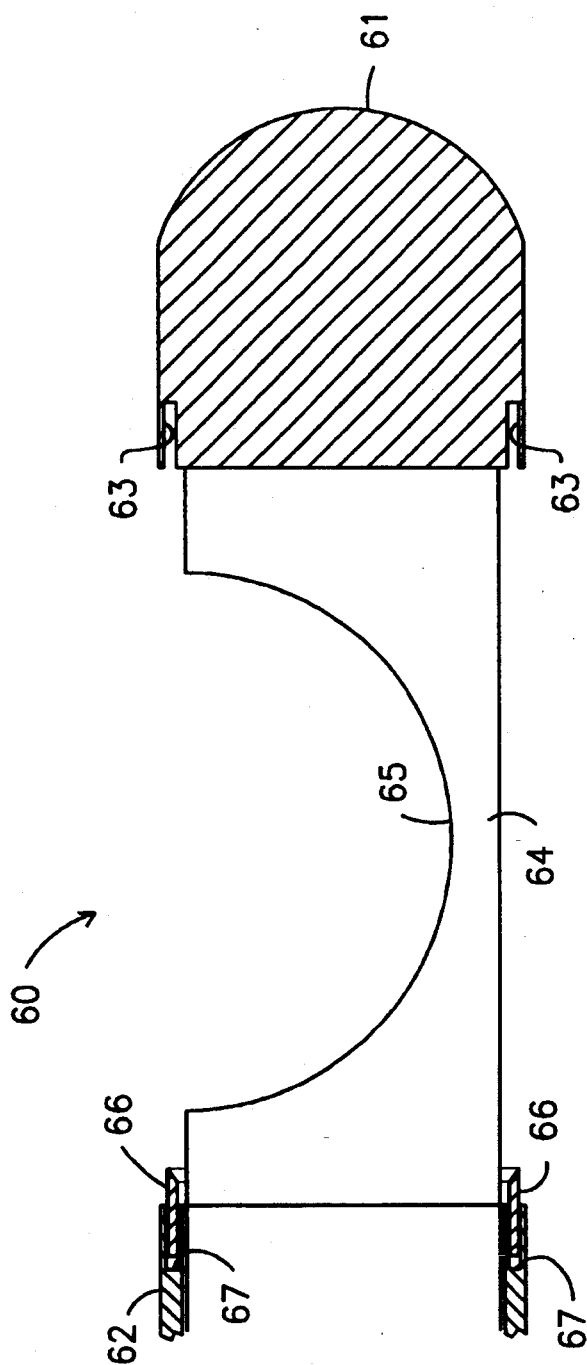
FIG. 4 is a sectional view of the distal, operative end of yet another embodiment of the atherectomy catheter particularly useful for removing fatty nodules.
Figure 5:
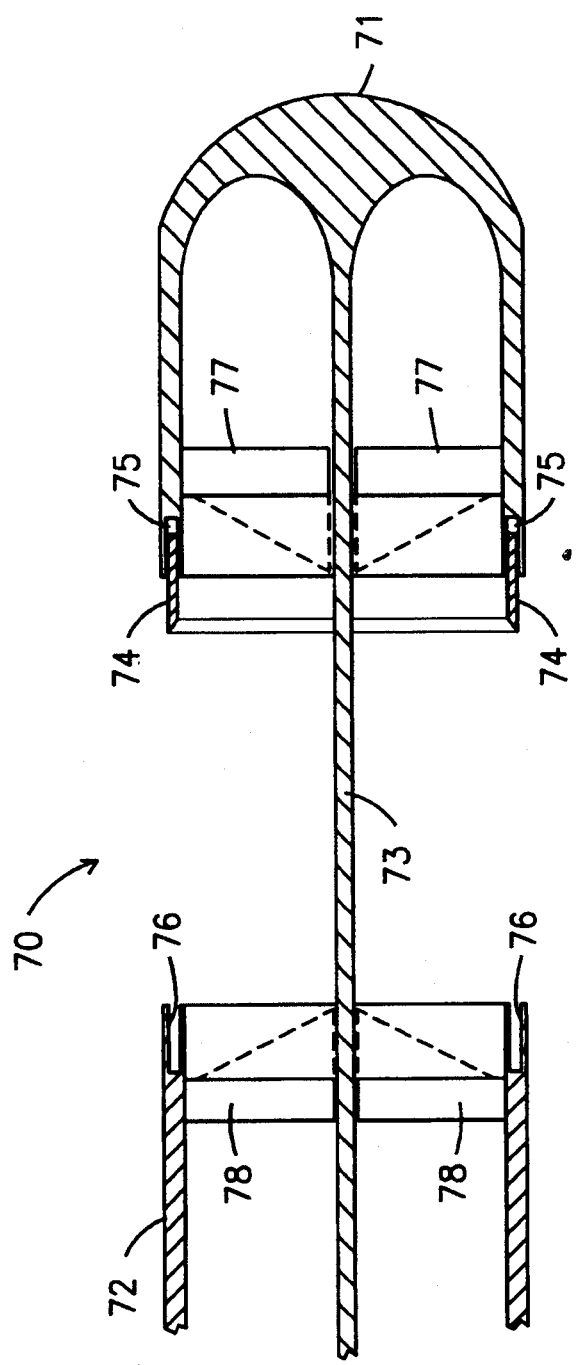
FIG. 5 is a sectional view of the distal, operative portion of still another embodiment of the atherectomy catheter also particularly suited for removing fatty nodules.
Figure 6:
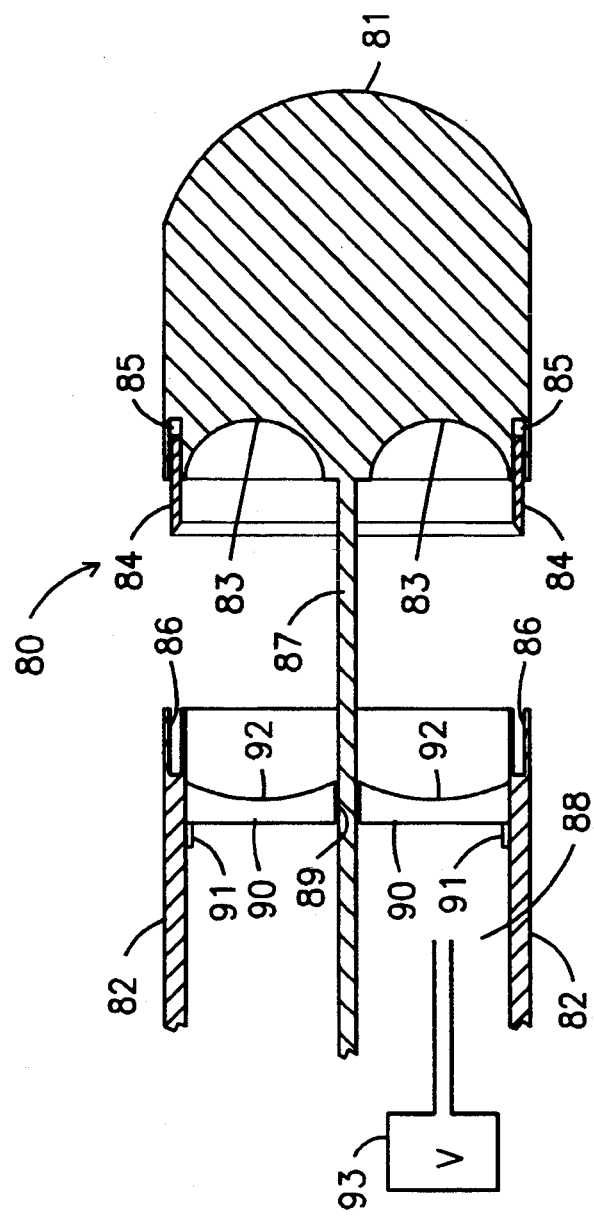
FIG. 6 is a sectional view of the distal, operative end of a final embodiment of the atherectomy catheter which is particularly suited for removing atherosclerosis along the length of an artery segment.

Referring now to the views of FIGS. 4, 5 and 6, additional embodiments for the atherectomy catheter of this invention are shown and generally indicated as 60, 70, and 80, respectively. Referring first to catheter 60 in the view of FIG. 4, one can see that catheter 60 defines a substantially hollow catheter body including a rigid tip 61 and a flexible segment 62. Tip 61 may be formed from any suitable material, as described above, and its specific size and configuration would depend upon the necessities of its intended use. It should be noted that catheter 60 of FIG. 4 is particularly designed and constructed for the removal of blockages caused by fatty nodules. For reasons discussed below, a cutting blade notch 63 is provided around a rearward portion of tip 61. Extending rearwardly from tip 61 is a cutting sleeve 64 which is fixedly attached to tip 61. Formed in cutting sleeve 64 is a cutting slot 65, the size and shape of which may be varied to best fit the blockage or nodule to be removed. In operation, cutting sleeve 64 is disposed in place just under the blockage or nodule to be removed in order to hold the mass once it has been severed, as will be described in greater detail below.

Flexible segment 62 is movably mounted for reciprocal movement along cutting sleeve 64 and comprises a circular blade ring 66 attached to the distal end thereof by blade ring receptor 67. From the view of FIG. 4, and due to the movable nature of segment 62 with regard to sleeve 64 and tip 61, one may see that upon closing catheter 60 by moving segment 62 toward tip 61, blade ring 66 would be received within the notch 63.

It is in this closed position that catheter 60 would be inserted into the patient's vessel from which the blockage or nodule is to be removed. Once the catheter 60 was properly positioned, flexible segment 62 would be moved rearwardly so that the nodule would be received within cutting slot 65. Then, flexible segment 62 would be moved forwardly into engagement with tip 61, resulting in severing of the nodule and its containment within slot 65 of the catheter 60. It is, of course, to be understood that the outside diameter of catheter 60, and certainly the outside diameter of sleeve 64, must not be greater than the inside diameter of the vessel from which the nodule is being removed in order not only to protect the vessel from the cutting action of blade ring 66, but also to prevent stretching of the vessel wall. In a preferred construction for catheter 60, blade ring receptor 67 would be threaded and the corresponding portion of blade ring 66 would also be threaded, permitting replacement of blade ring 66 without the necessity of discarding the entire catheter 60. Even though a threaded receptor 67 and ring 66 are preferred in this construction, other means for removably attaching blade ring 66 to segment 62 may be utilized. Finally, while the use of a vacuum means in combination with catheter 60 is not preferred, its use, substantially as previously described, is certainly within the scope of this invention.

Turning now to the view of FIG. 5, this catheter 70 may be referred to as a "full cut" fatty nodule catheter in that it is intended for use on any atherosclerosis, thrombosis, cholesterol deposits, fatty nodules, and other diseases that form blockages on all sides of the vessel. Catheter 70, like catheters 10 and 50, is particularly designed and constructed to remove such atherosclerosis from the entire inside diameter of the vessel in a single operation. As with the previous embodiments, catheter 70 comprises a substantially hollow body including a rigid tip 71 and a flexible segment 72. Tip 71 and segment 72 are connected one to the other by a center pull cable 73 such that tip 71 may be moved toward and away from segment 72 by reciprocal movement of cable 73. It is, therefore, to be understood that center pull cable 73 is formed from a substantially rigid material, and may be integral with tip 71 as shown in FIG. 5. A blade ring 74 is operatively disposed on the end of tip 71 adjacent segment 72, and is mounted to tip 71 by a corresponding blade ring receptor 75. A blade ring notch 76 is provided in the distal end of the segment 72 for receiving and enclosing blade ring 74 when catheter 70 is closed by retracting tip 71 into engagement with segment 72.

Proper relative placement and alignment between tip 71 and segment 72 is maintained by tip cable brace 77 and segment cable brace 78, through which cable 73 extends. In this preferred construction for catheter 70, both tip brace 77 and segment brace 78 are movably attached within their respective tips 71 and segments 72 so that the cavity defined therebetween, when catheter 70 is in its closed position, may be adjusted dependent upon the volume of atherosclerosis to be removed.

It is to be understood that catheter 10 would be positioned closed, with blade ring 74 received within and protected by notch 76 when catheter 70 is being inserted and moved to the location within the patient's vessel where a blockage is to be removed. Then, the device would be opened by advancing cable 73 to move tip 71 forwardly. This would not be done until catheter 70 had been positioned so that upon opening the atherosclerosis to be removed would fall within the space defined between the cutting edge of blade ring 74 and the distal end of segment 72. Having opened catheter 70, cable 73 would then be retracted, causing blade ring 74 to shave away the blockage and resulting in "capture" of the blockage fragments within the hollow body of catheter 70 between tip brace 77 and segment brace 78.

Finally, attention is invited to the view of FIG. 6 wherein a final embodiment of the atherectomy catheter of this invention has been generally designated as 80, and this catheter 80 may be conveniently identified as a length of vessel catheter. By this term, "length of vessel," it is meant to indicate that catheter 80 is especially designed and constructed for removing atherosclerosis from a significant longitudinal segment of a vessel in a single operation.

As with the previous embodiments, catheter 80 comprises a substantially hollow catheter body including a rigid tip 81 and a flexible segment 82. However, tip 81 is preferably of a solid, non-hollow construction, the proximal end of which includes a ring-like convex depression 83 formed therein. Operatively attached to the proximal end of tip 81 is a circular blade ring 84, and the attachment of blade ring 84 to tip 81 is accomplished by blade ring receptor 85. A blade ring notch 86 is formed around the distal lend of segment 82 for the purpose of receiving and enclosing blade ring 84 when catheter 80 is in its closed position.

Tip 81 and segment 82 are movably attached to each other by the center pull cable 87. Center pull cable 87 is fixedly attached to tip 81, and is preferably integrally formed therewith as shown in the view of FIG. 6. Of course, it can also be seen that center pull cable 87 extends rearwardly through the hollow body 88 of catheter 80 as defined by flexible segment 82. Accordingly, manipulating center pull cable 87 reciprocally will result in opening and closing of catheter 80 by moving tip 81 away from and toward flexible segment 82. Proper positioning and orientation between tip 81 and flexible segment 82 is maintained by passing cable 87 through a central aperture 89 formed through the axis of a secondary cutter means 90 which is attached to the interior wall of segment 82 within hollow body 88 by secondary cutter receptors 91. Secondary cutter 90 may be fixedly attached to receptors 91, or may be removably attached by the provision of mating threads or other suitable mechanical means. The secondary cutter 90 preferably comprises a plurality of spoke-like elements, the distal edges 92 thereof being sharpened.

Finally, a vacuum means 93 is operatively disposed in fluid-communicating relation to hollow body 88 so as to provide a negative pressure therein. In use, catheter 80 is closed and inserted into the patient's vessel using standard procedures and guide wire techniques. When tip 81 has passed the region of the vessel from which atherosclerosis is to be removed, cable 87 is extended, opening catheter 80 to expose blade ring 84. Then, the entire catheter 80 is retracted along a predetermined length of the vessel while negative pressure is applied within hollow body 88 through the action of vacuum means 33. As atherosclerosis is removed from the entire inside diameter of the vessel due to the shaving action of blade ring 84, removed material will be drawn across secondary cutter means 90 into hollow body 88. Secondary cutter means 90 is provided so as to more finely divide the removed material, and the removed material is actually directed toward secondary cutter means 90 and hollow body 88 by the convex depression 83 formed in the proximal end of tip 81.

The speed with which atherosclerosis is removed may be determined by the speed that catheter 80 is pulled back through the artery. The thickness of material extracted from the artery can be controlled not only by the outside diameter of catheter 80 but also by the degree to which tip 81 is extended distally away from flexible segment 82. It is also to be understood that by the application of greater negative pressure utilizing vacuum means 93, the quantity of atherosclerosis drawn into engagement with blade ring 84 will be increased. Once the desired removal of atherosclerosis has been completed, cable 87 is pulled rearwardly to close catheter 80, and the device is removed from the patient.

It will thus be seen that the objects set forth above, among those made apparent from the preceding description, are efficiently attained, and, since certain changes may be made in the above article without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An atherectomy catheter for the removal of atherosclerosis from within the blood vessels of a patient, said catheter comprising: a substantially hollow catheter body mounted on a guide wire, said guide wire and said catheter body being insertable into a vessel from which atherosclerosis is to be removed; said body comprising a substantially ridged tip and a flexible segment remote from said tip, said flexible segment being attached to said tip such that a circumferential gap is provided in said body between said tip and said flexible segment; and a cutting means operatively disposed in said circumferential gap such that manipulation of said body may cause said cutting means to remove atherosclerosis from the interior of the vessel and to direct the removed atherosclerosis into said hollow catheter body for disposal wherein said guide wire extends through said tip and said segment, and wherein said segment is attached to said tip by internal brace means, said cutting means being mounted to said tip by said internal brace means such that a cutting edge is disposed toward said flexible segment and is spaced apart therefrom in said circumferential gap.

2. An atherectomy catheter as in claim 1 further comprising means for applying a negative pressure to said hollow catheter body whereby the atherosclerosis will be drawn toward and at least partially into said circumferential gap.

3. An atherectomy catheter as in claim 1 wherein one of said tip and said segment is movable with respect to the other.

4. An atherectomy catheter as in claim 3 wherein said segment is movable with respect to said tip.

5. An atherectomy catheter as in claim 3 wherein said cutting means is mounted to said segment such that a cutting edge is disposed toward said tip.

6. An atherectomy catheter as in claim 3 wherein said tip is movable with respect to said segment.

7. An atherectomy catheter as in claim 6 wherein said cutting means is mounted to said tip such that a cutting edge is disposed toward said segment.

8. An atherectomy catheter as in claim 7 further comprising at least one secondary cutter mounted inside said hollow catheter body flexible segment such that atherosclerosis removed by said cutting means will be subdivided as it passes across said secondary cutter.

9. An atherectomy catheter as in claim 3 further comprising means for applying a negative pressure to said hollow catheter body whereby the atherosclerosis will be drawn toward and at least partially into said circumferential gap.

* * * * *